United States Patent [19]

McCarthy et al.

[11] Patent Number: 5,068,465

[45] Date of Patent: Nov. 26, 1991

[54] PHARMACEUTICALLY ACTIVE 3-ARYL-2-FLUORO-1-OLEFINS

[75] Inventors: James R. McCarthy, West Chester; Charlotte L. Barney, Cincinnati; Donald P. Matthews, West Chester, all of Ohio

[73] Assignee: Merrell Dow Pharmaceuticals Inc., Cincinnati, Ohio

[21] Appl. No.: 539,106

[22] Filed: Jun. 15, 1990

Related U.S. Application Data

[62] Division of Ser. No. 384,944, Jul. 25, 1989, Pat. No. 4,981,868.

[51] Int. Cl.$^5$ .................... C07C 39/10; C07C 39/24
[52] U.S. Cl. .................... 568/765; 549/82; 568/655; 568/766
[58] Field of Search ............ 568/655, 775, 780, 765, 568/766; 514/438, 445, ; 549/82

[56] References Cited

U.S. PATENT DOCUMENTS

| | | | |
|---|---|---|---|
| 3,850,997 | 11/1974 | Brossi et al. | 568/765 |
| 4,116,975 | 7/1990 | Klaus et al. | 549/81 |
| 4,981,868 | 1/1991 | McCarthy et al. | 514/430 |

OTHER PUBLICATIONS

J. McCarthy et al., Tetrahedron Letters, 31, No. 7, pp. 973–976, 1990.
The publication by Bey et al., J. Med. Chem., 27, 9 (1984).
M. Kolb et al., J. Med. Chem. 30, 267 (1987).
B. Rajashekhar et al., J. Biol. Chem., 259, No. 11, 6925 (1984).

*Primary Examiner*—Werren B. Lone
*Attorney, Agent, or Firm*—William J. Stein

[57] ABSTRACT

This invention relates to novel 3-aryl-2-fluoro-1-olefins and their pharmacological use as dopamine beta-hydroxylase DBH inhibitors in the treatment of DBH mediated conditions such as hypertension.

10 Claims, No Drawings

PHARMACEUTICALLY ACTIVE 3-ARYL-2-FLUORO-1-OLEFINS

This is a divisional of application Ser. No. 384,944, filed 07/25/89, U.S Pat. No. 4981,868.

BACKGROUND OF THE INVENTION

A need exists for compounds which inhibit the enzyme dopamine beta-hydroxylase (DMH). Research in the area of enzymatic inhibition has provided evidence that DBH facilitates the conversion of dopamine to norepinephrine in mammals. Inhibition of the enzyme (DBH) causes a decrease in the amount of norepinephrine produced which in turn effectuates, among other things, a lowering of blood pressure. DBH inhibitors are of value in the treatment of DBH mediated conditions such as, for example, hypertension.

Fluoro-substituted compounds are of interest due to their importance as pharmaceutical agents and as probes for understanding various metabolic and enzymatic processes. For example, P. Bey, et al, have disclosed 2-(3,4-dimethoxyphenyl)-3-fluoroallylamine, which is active as a monoamine oxidase inhibitor, in *J. Med. Chem.*, 27, 9 (1984), and M. Kolb, et al, have reported on monofluoroethenyl-GABA derivatives which are active as GABA-transaminase inhibitors, in *J. Med. Chem.*, 30, 267 (1987).

Although 2-bromo- and 2-chloro-3-(4-hydroxyphenyl)-1-propene compounds have been reported to be mechanism-based inhibitors of DBH in *J. Biol. Chem.*, 259, No. 11, 6925 (1984), apparently no vinyl fluoride compounds that are active as DBH inhibitors have heretofore been disclosed.

DESCRIPTION OF THE INVENTION

This invention relates to compounds of the formula

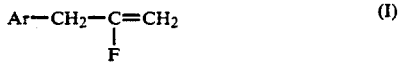

wherein Ar is selected from the group consisting of unsubstituted 3,4-dihydroxyphenyl, and optionally substituted 4-hydroxyphenyl, 4-($C_1$-$C_4$)alkoxyphenyl, 2-thienyl, and 3-thienyl, wherein the optional substituent is one or two substituent(s) selected from the group consisting of fluoro, chloro, bromo, ($C_1$-$C_4$)alkyl, and thio($C_1$-$C_4$)alkyl; and phenyl optionally substituted with one, two or three substituents selected from the group consisting of fluoro, chloro, bromo and thio($C_1$-$C_4$)alkyl.

These compounds are useful as DBH inhibitors in the treatment of, for example, hypertension. This invention also relates to methods of using the compounds of this invention, and to compositions containing these compounds.

The optional substituents can be attached to any of the Ar ring structures at any available carbon atom, and, in compounds having two or three substituents, the substituents may be the same or they may be different. The terms ($C_1$-$C_4$)alkyl and ($C_1$-$C_4$)alkoxy mean saturated or unsaturated, straight or branched chain alkyl or alkoxy groups having from one to four carbon atoms, and include such groups as methyl, ethyl, n-propyl, isopropyl, n-butyl, isobutyl, sec-butyl, tert-butyl, the corresponding alkoxy groups, and the like.

As is true for most classes of therapeutically effective compounds, certain subclasses and certain species which are especially effective are preferred over others. In this instance, those compounds of formula I wherein Ar is an optionally substituted 4-hydroxyphenyl, 2-thienyl and 3-thienyl are preferred.

The 2-fluoro-1-olefins of this invention can readily be prepared by following the reaction depicted in Reaction Scheme 1 below.

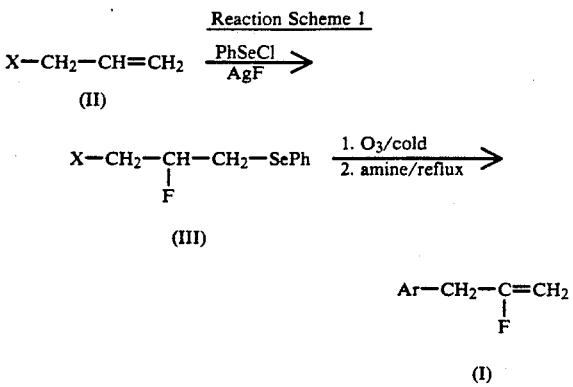

where X is 4-(4-methoxybenzyloxy)phenyl or any Ar group, PhSeCl is phenylselenyl chloride, AgF is silver fluoride, $O_3$ is ozone, and SePh is phenylselenide, and Ar is as described for formula I.

Generally, the compounds of this invention are made by reacting the appropriate compound (II) with phenylselenyl chloride (PhSeCl) and silver fluoride (AgF) in any aprotic solvent, preferably acetonitrile, to produce compound III. Then, at a temperature of about 25° C. (i.e., room temperature) to about −25° C., preferably at −15° C. to −25° C., compound III is treated with ozone in any chlorinated solvent such as, for example, methylene chloride, hexachloroethane, or, preferably, carbon tetrachloride. Treatment with ozone will, preferably, continue until the solution is saturated with ozone ($O_3$). Next, an appropriate amine, preferably diisopropylamine, is added to the solution and the solution is heated preferably at reflux for about one to about 48 hours, preferably for about 16 hours, to produce the compounds of formula I.

When converting a compound of formula II to its corresponding phenylselenide compound of formula III, the term "any aprotic solvent" means any solvent which neither donates nor accepts protons, and includes such solvents as dimethylformamide, benzene, dimethylsulfoxide, acetonitrile, propionitrile and the like. When converting a compound of formula III to its corresponding compound of formula I, the term "any chlorinated solvent" means any solvent that does not react with ozone, and includes such solvents as methylene chloride, carbon tetrachloride, hexachloroethane, and the like. When converting the phenylselenoxide compound of formula III to the corresponding product of formula I, the term "appropriate amine" means a non-nucleophilic amine, and includes such amines as triethylamine, diisopropyl amine, diazabicycloundecene (DBU), and the like.

When Ar is optionally substituted 4-hydroxyphenyl it is desirable to start with a protected phenol such as 4-(4-methoxybenzyloxy)phenyl or tetrahydrofuranyl, as the X component in the compound of formula II, and to proceed through the reaction of Scheme 1 until the selenoxide compound of formula III has been treated with an appropriate amine at reflux. Then the protecting group is removed with saturated methanolic hydrochloric acid to leave the desired fluorinated 4-hydroxyphenyl compound.

Starting materials, that is, the compounds of formula II, are either readily available, or they can be synthesized. Synthesis of the compounds wherein X is an optionally substituted phenyl group can be accomplished by following a procedure set forth in *J. Am. Chem. Soc.*, 100, 5800, (1978), or *Organomet.*, 1, 259 (1982). Synthesis of the compounds wherein X is an optionally substituted phenyl group or an optionally substituted thienyl group can be accomplished by following a procedure set forth in *J. Amer. Chem. Soc.*, 90(20), 5531 (1968).

The following specific examples are presented to illustrate the synthesis of the compounds of this invention, but they should not be construed as limiting the scope of this invention in any way.

EXAMPLE 1

3-(4-Methoxyphenyl)-2-Fluoro-1 (Phenylselenyl)-Propane (III)

Finely ground silver fluoride (glove bag), dry acetonitrile (100 ml), and phenylselenenyl chloride (4.6 g, 24 mmole) were added to a dry 250 ml flask equipped with septum and argon bubbler. 4-Allylanisole (II) (Ar=4-methoxyphenyl) (2.96 g, 20 mmole), dissolved in 25 ml acetonitrile, was added via syringe. The reaction was stirred at room temperature for 18 hours, after which time the reaction was filtered through a celite pad and treated with about 15 ml flash silica gel. The mixture was evaporated to a powder at less than 30° C., and the title compound was separated out by flash chromatography (10% ether in hexane). The product (3.39 g, 53%) was obtained as white crystals.

M.p. 20°-23° C. $^1$H NMR (300 MHz, CDCl$_3$) δ 2.90-3.19 (m, 4), 3.79 (s, 3), 4.80 (dm, 1, J=47.6 Hz), 6.83 (d, 2, J=8.7 Hz), 7.10 (d. 2, J=8.7 Hz), 7.25 (m, 3), 7.50 (m, 2), $^{19}$F NMR (CDCl$_3$) δ (vs. CFCl$_3$, 282 MHz)−171.6 (dtt, J=46.2, 27, 21 Hz); MS (CI/CH$_4$) m/z 325 (MH$^+$ for $^{80}$Se). Anal. Calcd. for C$_{16}$H$_{17}$FOSe: C, 59.44; H, 5.30. Found: C, 59.50; H, 5.29

EXAMPLE 2

3-(4-Methoxyphenyl)-2-Fluoro-1-Propene (I)

A solution of the compound of example 1 (1.0 g, 3 mmol) in carbon tetrachloride (100 ml) was cooled to −20° C., and ozone was bubbled through the solution until a light blue color persisted. Diisopropylamine (0.6 g, 6 mmol) was added and the solution was heated at reflux for 16 hours, washed with ice cold dilute hydrochloric acid (2 times at 50 ml each), aqueous sodium carbonate (50 ml) and dried over magnesium sulfate. The solution was evaporated to an oil and purified by flash chromatography (hexane) to provide 415 mg (83%) of 3-(4-methoxyphenyl)-2-fluoro-1-propene as a colorless oil. Kugelrohr distillation of a small sample at 50°-60° C. (0.05 mm) provided analytically pure 3-(4-methoxyphenyl)-2-fluoro-1-propene.

$^1$H NMR (300 MHz, CDCl$_3$) δ 3.43 (d, 2, J=14.9 Hz), 3.80 (s, 3), 4.21 (ddt, 1, J=49.4, 2.8, 0.9 Hz) 4.58 (dd, 1, J=16.8, 2.7 Hz) 6.86 (d, 2, J=8.7 Hz), 7.17 (d, 2, J=8.7 Hz); $^{19}$F NMR (CDCl$_3$) δ (vs. CFCl$_3$, 282 MHz) −95.0 (ddt, J=49.1, 15.8, 15.2 Hz); MS CI/CH$_4$) m/z 167 (MH$^+$). Anal. Calcd. for C$_{10}$H$_{11}$FO: C, 72.27; H, 6.67. Found C, 72.33; H, 6.78.

EXAMPLE 3

4-Allyl-1-(4-Methoxybenzyloxy)Benzene (II)

4-Allylphenol, (6.14 g, 0.046 moles), 4-methoxybenzyl chloride, (6.3 ml, 0.046 moles), potassium carbonate (8.3 g, 0.06 moles) and a catalytic amount of potassium iodide were mixed together in about 200 ml acetone, and heated to reflux, with stirring. The reaction was allowed to proceed overnight, then cooled to room temperature and diluted with about 100 ml water. The product was extracted into ethyl acetate (3 times, 300 ml each time), and then dried over magnesium sulfate/potassium carbonate, filtered and concentrated in vacuo to yield the title compound as a light yellow solid, m.p. 59°-61° C.

EXAMPLE 4

3-(4-Methoxybenzyloxyphenyl)-2-Fluoro-1-(Phenylselenyl)Propane (III)

Phenylselenium chloride (1.81 g, 9.432 mmole) and 2.5 g (19.65 mmole) silver fluoride (glove bag) were each weighed into separate oven-dried, single necked flasks under nitrogen. Acetonitrile (15 ml) was added to each flask. Two grams of the compound of example 3 was dissolved in 15 ml acetonitrile and added to the flask containing silver fluoride. The phenylselenium chloride was added next, the reaction was stirred at room temperature overnight. The reaction was filtered through a small amount of silica gel, eluted with chloroform and concentrated under reduced pressure to yield 2.94 g oil. Purification by flash chromatography (10% ether/hexane) produced 1.83 g white solid (yield of 64.3%).

Anal. Calcd. for C$_{23}$H$_{23}$FO$_2$Se: C, 64.33; H, 5.40. Found for C$_{23}$H$_{23}$FO$_2$Se: D, 64.42; 5.37.

EXAMPLE 5

3-(4-Methoxybenzyloxyphenyl)-2-Fluoro-1-Propene

In a manner similar to that described in example 2, 1.37 g (3.19 mmole) of the compound of example 4 was dissolved in 100 ml carbon tetrachloride, cooled to −20° C., and treated with ozone until a blue color persisted. The reaction was quenched with 323 mg (3.19 mmole) diisopropylamine and refluxed overnight. Purification by flash chromatography (20% ether/hexane) gave 387 mg (66.4% title compound based on recovered starting material.

Anal. Calcd. for C$_{17}$H$_{17}$FO$_2$: C, 74.97, H, 6.29. Found for C$_{17}$H$_{17}$FO$_2$: C, 74.50, 74.32; H, 6.10, 6.23. m.p. 77°-78° C.

EXAMPLE 6

3-(4-Hydroxyphenyl)-2-Fluoro-1-Propene (I)

3-(4-Methoxybenzyloxyphenyl)-2-fluoro-1-propene, i.e., the compound of example 5, (30 mg, 0.110 mmole) was treated with saturated methanolic hydrochloric acid and stirred at room temperature for one hour. The solution was then poured onto 50 ml cold saturated sodium chloride, diluted with 20 ml ether and the pH adjusted to pH 10 with cold 0.5N sodium hydroxide. The mixture was washed 3 additional times with 15 ml portions of 0.5N sodium hydroxide, and the combined aqueous layers were then washed with 50 ml ether. The aqueous layers were then acidified with 1.0N hydrochloric acid to pH 1, solid sodium chloride added and the product extracted with ether (3×50 ml), dried(M- gSO₄) and concentrated under reduced pressure to give 8 mg clear oil (48%).

¹H NMR (300 MHz, CDCl₃) δ 3.42 (d, 2, J=15 Hz), 4.22 ddt, 1, J=46.5, 2.1, 0.6 Hz), 4.61 (dd, 1, J=16.8, 2.7 Hz), 6.79 (d, 2, J=8.4 Hz), 7.12 d, 2, J=8.7 Hz); ¹⁹F NMR (CDCl₃) (vs. CFCl₃ 282 MHz) −95.05 (ddt, J=6.64,49.1 15.2 Hz) MS (CI/CH₄) m/z 153 (MH+) HRMS Calcd. for C₉H₉FO: 152.0367. Found 152.0636.

In a like manner, by substituting the following compounds for 4-allylanisole (i.e., a compound of formula II) and by following the procedure set forth in examples 1 and 2, the following compounds can be made:

3,5-di(4-methoxybenzyloxy)allylbenzene to yield 3-(3,5-dihydroxyphenyl)-2-fluoro-1-propene;
allylbenzene to yield 3-phenyl-2-fluoro-propylene;
2-allylthiophene to yield 3-(2-thiophenyl)-2-fluoro-1-propene;
3-allylthiophene to yield 3-(3-thiophenyl)-2-fluoro-1-propene;
3-fluoro-1-allylbenzene to yield 3-(3-fluorophenyl)-2-fluoro-1-propene;
3,5-dimethyl-4-methoxy-1-allylbenzene to yield 3-(3,5-dimethyl-4-methoxyphenyl)-2-fluoro-1-propene;
4-allyl-2-methylthioanisole to yield 3-(4-methylthio-3-methyl)-2-fluoro-1-propene;
4-allyl-3-methylanisole to yield 3-(2-methyl-4-methoxyphenyl)-2-fluoro-1-propene;
5-methyl-2-allylthiophene to yield 3-(5-methyl-2-thienyl)-2-fluoro-1-propene;
5-chloro-3-allylthiophene to yield 3-(5-chloro-3-thienyl)-2-fluoro-1-propene;
4-allylthioanisole to yield 3-(4-thiomethylphenyl)-2-fluoro-1-propene;
4-chloro-1-allylbenzene to yield 3-(4-chlorophenyl)-2-fluoro-1-propene;
2,5-dichloro-3-allylthiophene to yield 3-(2,5-dichloro-3-thienyl)-2-fluoro-1-propene;
3,5-dimethyl-1-allylbenzene to yield 3-(3,5-dimethylphenyl)-2-fluoro-1-propene;
2-chloro-4-allyltoluene to yield 3-(4-methyl-3-chlorophenyl)-2-fluoro-1-propene;
3-fluoro-4-(4-methoxybenzyloxy)allylbenzene to yield 3-(3-fluoro-4-hydroxyphenyl)-2-fluoro-1-propene;
5-bromo-2-allylthiophene to yield 3-(5-bromo-2-thienyl-2-fluoro-1-propene;
3,4-di(4-methoxybenzyloxy)allylbenzene to yield 3-(3,4-dihydroxyphenyl)-2-fluoro-1-propene;
3,5-difluoro-4-(4-methoxybenzyloxy)allylbenzene to yield 3-(3,5-difluoro-4-hydroxyphenyl)-2-fluoro-1-propene.

Also, by substituting the following starting materials for 4-allyl phenol of example 3, and by following the procedure set forth in examples 3 through 6, the following compounds can be made:

3-methyl-4-(4-methoxybenzyloxy)allylbenzene to yield 3-(3-methyl-4-hydroxyphenyl)-2-fluoro-1-propene;
3-methylthio-4-(4-methoxybenzyloxy)allylbenzene to yield 3-(3-thiomethyl-4-hydroxyphenyl)-2-fluoro-1-propene.
3,5-dichloro-4-(4-methoxybenzyloxy)allylbenzene to yield 3-(3,5-dichloro-4-hydroxyphenyl)-2-fluoro-1-propene;

The compounds of this invention are useful as dopamine beta-hydroxylase inhibitors for the treatment of, for instance, hypertension. The dopamine beta-hydroxylase (DBH) inhibitory properties of the compounds of this invention can readily be determined by standard and well known procedures. For example, determination of whether DBH inhibition demonstrates time-dependent kinetics is exemplified by a procedure wherein enzymatic oxygenation by DBH is determined in aqueous solution in the presence of molecular oxygen, an electron donor such as ascorbate, and the necessary cofactors for the enzyme at a pH of about 5, and at a temperature of about 37° C. The test compound is added at the desired concentration, and the system is incubated. At different time intervals, tyramine, a substrate of DBH, is introduced to aliquots of the incubated enzyme solution and DBH activity is measured by the method of S. May, et al, *J. Biol. Chem.* 256, 2258 (1981), where the enzyme-activated conversion of tyramine is followed by monitoring oxygen uptake by means of a polarographic electrode and an oxygen monitor, to determine the level of DBH activity. In tests utilizing the above described procedure, the DBH inhibitory activity of the test compound increased as a function of the time of incubation, as indicated in Table I.

TABLE I

| TIME-DEPENDENT DBH INHIBITORY ACTIVITY | | |
|---|---|---|
| Compound | Concentration | t ½ |
| 3-(4-Hydroxyphenyl)-2-Fluoro-1-Propene | 12.9 mM | 5 min. * | t ½: time required to reach 50% log activity
* 0.989 correlation

Through standard toxicity tests and by standard pharmacological assays for the determination of antihypertensive activity in mammals, and by comparison of these results with known antihypertensive agents, the effective antihypertensive dosage of the compounds of this invention to be administered to patients can readily be determined. A patient, for the purpose of this invention, is a mammal, including a human, in need of treatment for a particular condition, injury or disease, such as hypertension.

The amount of active ingredient (i.e., a compound of Formula I) to be administered to a patient for the treatment of hypertension can vary widely according to such considerations as the particular compound and dosage unit employed, the period of treatment, the age and sex of the patient treated, and the extent of the hypertension treated.

The total amount of active ingredient to be administered intravenously will generally range from about 0.1 mg/kg to 30 mg/kg and preferably from 1.0 mg/kg to 10.0 mg/kg. A unit dosage may contain from 5 mg to 525 mg of active ingredient, and can be taken one or more times per day. For example, a 50 kg patient may be administered 50 mg–700 mg active ingredient four times a day for a total dose of 200 mg–2800 mg per day.

The total amount of active ingredient to be administered orally will generally range from 0.1 mg/kg to 100 mg/kg, and preferably from 1.0 mg/kg to 50 mg/kg. A unit dosage may contain from 5 mg to 1000 mg of active ingredient, and can be taken one or more times per day. For example, a 50 kg patient may be administered 50 mg–2500 mg of active ingredient four times a day for a total of 200 mg–10,000 mg per day.

The compounds of this invention can be utilized to achieve the desired pharmacological effect by administration to a patient in need thereof in an appropriately formulated pharmaceutical composition. Therefore, the present invention includes pharmaceutical compositions which are comprised of a pharmaceutically-acceptable carrier and a pharmaceutically-effective amount of a compound of Formula I. A pharmaceutically-acceptable carrier is any carrier which is relatively non-toxic and innocuous to a patient at concentrations consistent with effective activity of the active ingredient so that any side effects ascribable to the carrier do not vitiate the beneficial effects of the active ingredient. A pharmaceutically-effective amount of compound is that amount which produces a result or exerts an influence on the particular condition being treated. The compounds of Formula I can be administered with a pharmaceutically-acceptable carrier using conventional dosage unit forms orally, parenternally, topically, as an aerosol, or the like.

For oral administration the compounds can be formulated into solid or liquid preparations such as capsules, pills, tablets, troches, lozenges, melts, powders, solutions, suspensions, or emulsions and may be prepared according to methods known to the art for the manufacture of pharmaceutical compositions. The solid unit dosage forms can be a capsule which can be of the ordinary hard- or soft-shelled gelatin type containing, for example, surfactants, lubricants, and inert fillers such as lactose, sucrose, calcium phosphate, and cornstarch.

In another embodiment, the compounds of this invention may be tableted with conventional tablet bases such as lactose, sucrose, and cornstarch in combination with binders such as acacia, cornstarch, or gelatin, disintegrating agents intended to assist the break-up and dissolution of the tablet following administration such as potato starch, alginic acid, corn starch, and guar gum, lubricants intended to improve the flow of tablet granulations and to prevent the adhesion of tablet material to the surfaces of the tablet dies and punches, for example, talc, stearic acid, or magnesium, calcium, or zinc stearate, dyes, coloring agents, and flavoring agents intended to enhance the aesthetic qualities of the tablets and make them more acceptable to the patient. Suitable excipients for use in oral liquid dosage forms include diluents such as water and alcohols, for example, ethanol, benzyl alcohol, and the polyethylene alcohols, either with or without the addition of a pharmaceutically acceptably surfactant, suspending agent, or emulsifying agent.

The compounds of this invention may also be administered parenterally, that is, subcutaneously, intravenously, intramuscularly, or interperitoneally, as injectable dosages of the compound in a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,3-dioxolane-4-methanol, ethers such as poly(ethyleneglycol) 400, an oil, a fatty acid, a fatty acid ester or glyceride, or an acetylated fatty acid glyceride with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutically adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example, dimethyl dialkyl ammonium halides, alkyl pyridinium halides, and alkylamines acetates; anionic detergents, for example, alkyl, aryl, and olefin sulfonates, alkyl, olefin, ether, and monoglyceride sulfates, and sulfosuccinates; nonionic detergents, for example, fatty amine oxides, fatty acid alkanolamides, and polyoxyethylenepolypropylene copolymers; and amphoteric detergents, for example, alkyl-beta-aminopropionates, and 2-alkylimidazoline quaternary ammonium salts, as well as mixtures.

The parenteral compositions of this invention will typically contain from about 0.5% to about 25% by weight of the active ingredient in solution. Preservatives and buffers may also be used advantageously. In order to minimize or eliminate irritation at the site of injection, such compositions may contain a non-ionic surfactant having a hydrophile-lipophile balance (HLB) of from about 12 to about 17. The quantity of surfactant in such formulations ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents which may be a naturally-occurring phosphatide such as lecithin, a condensation product of an alkylene oxide with a fatty acid, for example, polyoxyethylene stearate, a condensation product of ethylene oxide with a long chain aliphatic alcohol, for example, heptadecaethyleneoxycetanol, a condensation product of ethylene oxide with a partial ester derived from a fatty acid and a hexitol such as polyoxyethylene sorbitol monooleate, or a condensation product of an ethylene oxide with a partial ester derived from a fatty acid and a hexitol anhydride, for example, polyoxyethylene sorbitan monooleate.

The suspensions may also contain one or more preservatives, for example, ethyl or n-propyl p-hydroxybenzoate; one or more coloring agents; one or more flavoring agents; and one or more sweetening agents such as sucrose or saccharin.

Oily suspensions may be formulated by suspending the active ingredient in a vegetable oil such as, for example, arachis oil, olive oil, sesame oil or coconut oil, or in a mineral oil such as liquid paraffin. The oily suspensions may contain a thickening agent such as, for example, beeswax, hard paraffin or cetyl alcohol. The sterile injectable preparation may also be a sterile injectable solution or suspension in a non-toxic parenterally-acceptable diluent or solvent. Diluents and solvents that may be employed are, for example, water, Ringer's solution, and isotonic sodium chloride solution. In addition, sterile fixed oils are conventionally employed as solvents or suspending media. For this purpose, any bland, fixed oil may be employed including synthetic mono- or diglycerides. In addition, fatty acids such as oleic acid can be used in the preparation of injectables.

A composition of the invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are, for example, cocoa butter and polyethylene glycol.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example those sweetening, flavoring, and coloring agents described above, may also be present.

The compounds of this invention may be formulated as solutions, suspensions, emulsions, powders, and semi-solid preparations administered as an aerosol preparation by means of a pressurized aerosol container together with a gaseous or liquefied propellant such as, for example, dichlorodifluoromethane, dichlorodifluoromethane with dichlorodifluoroethane, carbon dioxide, nitrogen, propane, or the like, with the usual adjuvants such as co-solvents and wetting agents, as may be necessary or desirable. The compounds may also be administered in a non-pressurized form such as in a nebulizer or atomizer. The aerosols are intended for administration as fine, solid particles or as liquid mists via the respiratory system, and the particle size of aerosol preparations intended for administration to the lungs should be below 50 micrometers, in most instances.

The pharmaceutical compositions of the invention may also be in the form of oil-in-water emulsions. The oily phase may be a vegetable oil such as liquid paraffin or a mixture of vegetable oils. Suitable emulsifying agents may be (1) naturally-occurring gums such as gum acacia and gum tragacanth, (2) naturally-occurring phosphatides such as soy bean and lecithin, (3) esters or partial esters derived from fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Syrups and elixirs may be formulated with sweetening agents such as, for example, glycerol, propylene glycol, sorbitol or sucrose. Such formulations may also contain a demulcent, and preservative and flavoring and coloring agents.

The compositions of the invention can also contain other conventional pharmaceutically-acceptable compounding ingredients, generally referred to as carriers or diluents, as necessary or desired. Any of the compositions of this invention may be preserved by the addition of an antioxidant such as ascorbic acid or by other suitable preservatives. Conventional procedures for preparing such compositions in appropriate dosage forms can be utilized.

The following specific examples are presented to illustrate compositions of this invention, but they should not be construed as limiting the scope of this invention in any way.

EXAMPLE 7

A tablet is prepared from 3-(4-Methoxyphenyl)2-fluoro-1propene

| 1-propene | 250 mg |
| Starch | 40 mg |
| Talc | 10 mg |
| Magnesium | 10 mg |

EXAMPLE 8

A capsule is prepared from 3-(4-Hydroxyphenyl)2-fluoro-1-propene

| 1-propene | 400 mg |
| Talc | 40 mg |
| Sodium Carboxymethyl Cellulose | 40 mg |
| Starch | 120 mg |

The compounds of this invention may also be utilized in research and diagnostics or as analytical references or standards, and the like. Therefore, the present invention includes general compositions which are comprised of an inert carrier and an effective amount of a compound of Formula I, or a salt thereof. An inert carrier is any material which does not interreact with the compound to be carried and which lends support, means of conveyance, bulk, traceable material, and the like to the compound to be carried. An effective amount of compound is that amount which produces a result or exerts an influence on the particular procedure being performed.

It should be apparent to one of ordinary skill in the art that changes and modifications can be made to this invention without departing from the spirit or scope of the invention as it is set forth herein.

We claim:

1. A compound of the formula

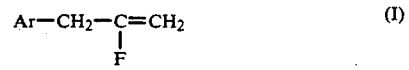

wherein Ar is 3,4-dihydroxyphenyl, 4-hydroxyphenyl, 4-($C_1$-$C_4$) alkoxyphenyl or substituted phenyl, wherein the substituents on the phenyl group are selected from the group consisting of fluoro, chloro, bromo and ($C_1$-$C_4$) alkyl.

2. A compound of claim 1 wherein Ar is, 4-hydroxyphenyl or 4-methoxyphenyl.

3. A compound of claim 1 wherein Ar is substituted phenyl.

4. A compound of claim 1 which is 3-(4-hydroxyphenyl)-2-fluoro-1-propene.

5. A compound of claim 1 which is 3-(4-methoxyphenyl)-2-fluoro-1-propene.

6. A compound of claim 1 which is 3-(3,4-dihydroxyphenyl)-2-fluoro-1-propene.

7. A method of treating hypertension which comprises administering to a patient in need thereof a compound of the

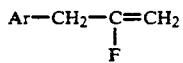 (I)

wherein Ar is 3,4-dihydroxyphenyl, 4-hydroxyphenyl, 4-($C_1$–$C_4$) alkoxyphenyl or substituted phenyl, wherein the substituents on the phenyl group are selected from the group consisting of fluoro, chloro, bromo and ($C_1$–$C_4$) alkyl.

8. A method of treating hypertension according to claim 7 wherein the compound if 3-(3,4-dihydroxyphenyl phenyl)-2-fluoro-1-propene.

9. A method of producing a vasodilitory effect in a patient in need thereof through the administration of a pharmaceutically-effective amount of a compound of claim 1.

10. A pharmaceutical composition comprising an effective amount of a compound of claim 1 in combination with a pharmaceutically-acceptable carrier.

* * * * *